United States Patent [19]

Hrushesky

[11] Patent Number: 4,519,395

[45] Date of Patent: May 28, 1985

[54] MEDICAL INSTRUMENT FOR NONINVASIVE MEASUREMENT OF CARDIOVASCULAR CHARACTERISTICS

[76] Inventor: William J. M. Hrushesky, 5049 Colfax Ave. South, Minneapolis, Minn. 55419

[21] Appl. No.: 450,066

[22] Filed: Dec. 15, 1982

[51] Int. Cl.³ .............................................. A61B 5/02
[52] U.S. Cl. ................................... 128/671; 128/905; 128/700
[58] Field of Search ............................... 128/670–671, 128/687–690, 905, 700

[56] References Cited

U.S. PATENT DOCUMENTS

| | | | |
|---|---|---|---|
| 3,661,147 | 5/1972 | Mason et al. | 128/689 |
| 4,281,663 | 8/1981 | Pringle | 128/689 |
| 4,338,950 | 7/1982 | Barlow, Jr. et al. | 128/687 |
| 4,355,644 | 10/1982 | Saito | 128/689 |

OTHER PUBLICATIONS

Akselrod, S., et al., "Power Spectrum Analysis of Heart Rate Fluctuation: a Quantitative Probe of Beat-to-Beat Cardiovascular Control", *Science* 213:220–222, 1981.

Williams, A., Gropper, A., "Interrelationships of Cardiac Output, Blood Pressure, and Peripheral Resistance During Normal Respiration in Normotensive and Hypertensive Individuals", *Circulation* 4:278–286, 1951.

Chess, G., Tam, R., Calaresco, F., "Influence of Cardiac Neural Inputs on Rhythmic Variations of Heart Period in the Cat", *Am. J. of Physiology* 228:775–781, 1975.

Womak, B., "The Analysis of Respiratory Sinus Arrhythmia Using Special Analysis and Digital Filtering", *IEEE Transactions on Biomedical Engineering* 18:399–409, 1971.

Flaherty, J., "Influence of Respiration on Recording Cardiac Potentials", *Am. J. of Cardiology* 20:21–28, 1967.

Fischmann, E., et al., "Beat to Beat and Observer Variation of the Electrocardiogram", *American Heart Journal* 75:465–473, 1968.

Lauson, H., et al., "The Influence of the Respiration on the Circulation in Man", *Am. J. of Medicine* 1:315–336, 1946.

(List continued on next page.)

*Primary Examiner*—Lee S. Cohen
*Assistant Examiner*—Angela D. Sykes
*Attorney, Agent, or Firm*—Kinney & Lange

[57] ABSTRACT

A medical instrument includes a noninvasive pulse transducer which senses heart beats of a human subject. Based upon pulse signals from the transducer, the instrument provides visual stimulae which allow the human subject to voluntarily synchronize the subject's respiration cycles with the subject's heart beats. At the same time, the instrument determines and stores the instantaneous beat-to-beat heart rate for each beat of the respiratory cycles. After a predetermined number of synchronized respiratory cycles have been completed, the instrument performs both classical statistical and rhythmometric analyses utilizing the stored instantaneous heart rates. The instrument determines from these analyses mean and standard error values for each beat of the respiratory cycle; an analysis of variance of the mean value; a rhythm qualified mean heart rate value; an amplitude value; a timing value (which indicates the location of the peak of the cosine curve best fitting the heart rate data within the respiratory cycle), and a percent rhythm value (which indicates the quality of the fit with the cosine curve to the stored instantaneous heart rates). The amplitude value provides an indication of the physiological (as opposed to chronological) cardiovascular age of the human subject, since it indicates the compliance of the heart tissue. The effect of cardiotoxins, cardiac drugs, other substances, as well as altered physiologic states upon a subject's heart tissue compliance also can be monitored using the amplitude, mean and peak timing values produced by the instrument. The instrument provides a displayed and/or printed output so that the subject or his or her physician has a simple yet accurate indication of heart condition which may be evaluated periodically and followed over time.

35 Claims, 8 Drawing Figures

OTHER PUBLICATIONS

Starr, I., et al., "On the Cause of the Respiratory Variation of the Ballistocardiogram, with a Note on Sinus Arrhythmia", *J. of Clin. Investiation* 25:53-64, 1946.

Bainbridge, F. A., "The Relationship Between Respiration and the Pulse Rate", *J. Physiol.* 54:192-202, 1920.

Almasi, J., Schmitt, O., "Basic Technology of Voluntary Cardiorespiratory Synchronization in Electrocardiology", *IEEE Transactions on Biomedical Engineering* 21:264-273, 1974.

Sokal, R. et al., *Biometry, The Principles and Practice of Statistics in Biological Research,* Chapters 4 and 8, (1969).

Cornelissen, G., et al., "Chronobiometry with Pocket Calculators and Computer Systems", *La Ricerca Clin. Lab.,* 10, 333, (1980).

Halberg, F., "Auto-rhythmometry Procedures for Physiologic Self-measurements and Their Analysis", *Phsiol. Teach.* 1:1-11, (1972).

Hotelling, H., *Annals of Mathematical Statistics,* vol. 2, p. 360, (1931).

MEDICAL INSTRUMENT FOR NONINVASIVE MEASUREMENT OF CARDIOVASCULAR CHARACTERISTICS

BACKGROUND OF THE INVENTION

1. Field of the Invention

The present invention relates to an apparatus and method for measurement of a cardiovascular function. In particular, the present invention relates to a totally noninvasive, quick and simple medical instrument for measurement of cardiovascular characteristics during voluntary cardiorespiratory synchronization.

2. Description of the Prior Art

Despite the extensive research relating to the cardiovascular system and despite the development of sophisticated electromedical instrumentation, there is a continuing need for a simple, reliable, noninvasive and rapid method of providing an indication of the condition of the cardiovascular system. At the present time, the most commonly used type of equipment is the electrocardiogram (EKG), in which several electrodes are attached to the subject and the signals are amplified and used to generate an electrocardiogram. The interpretation of an electrocardiogram requires a skilled physician, who must make a number of qualitative as well as quantitative decisions to determine whether or not the subject's cardiovascular system is within a normal range. The electrical signals comprising the EKG record convey information which is strictly limited to the electrical activity of the cardiovascular tissue. While changes in the depolarization and repolarization patterns of cardiac tissue are associated with certain pathological conditions, no direct physiologic information is available from the EKG record. A simpler, easier-to-use system which provides a more direct information about the physiologic cardiovascular condition would be highly desirable.

Two and one-half centuries ago, Stephen Hales documented respiratory influences upon the circulatory system. Hales, S., *Statical Essays, Vol. II Haemastaticks.* (Innins and Manby, London, 1733). In 1847, Karl Ludwig recorded concurrent heart rate, respiratory pattern, and blood pressure in a dog and noted that during inspiration the heart rate increased and blood pressure fell while the opposite occurred during expiration. Ludwig, F. W. "Beitrage zur Kenntniss des Einflusses der Respirations-bewequngen auf den Blutlauf im Aortensysteme". *Achiv fur Anatomie und Phsyiologie,* 261, 1847. Over the years, the misnomer "sinus arrhythmia" (S.A.) has been attached to this ryhthmic phenomenon of pulse quickening upon inspiration and slowing upon expiration. Hering, E., "Uber eine reflectorische Beziehung zwischen Lunge und Herz". *Sitzber. Akad. Wiss. Wien.* 64:333–353, 1871.

The precise causes of this relationship have been investigated since these early observations. The proposed mechanism include: rhythmically changing sympathetic and parasympathetic nervous balance; respiratory phase-dependent changes in blood chemistry; and recurrent breathing-dependent changes in the intrathoracic pressure. These rhythmic pressure changes affect cardiac filling. Akselrod, S., et al., "Power Spectrum Analysis of Heart Rate Fluctuation: a Quantitative Probe of Beat-to-Beat Cardiovascular Control", *Science* 213:220–222, 1981. Williams, A., Copper, A., "Interrelationships of Cardiac Output, Blood Pressure, and Peripheral Resistance During Normal Respiration in Normotensive and Hypertensive Indiviudals", *Circulation* 4:278–286, 1951. Chess, G., Tam, R., Calaresco, F, "Influence of Cardiac Neural Inputs on Rhythmic Variations of Heart Period in the Cat", *Am. J. of Physiology* 288:775–781, 1975. Womak, B., "The Analysis of Respiratory Sinus Arrhythmia Using Special Analysis and Digital Filtering", *IEEE Transactions on Biomedical Engineering* 18:339–409, 1971. Flaherty, J., "Influence of Respiration on Recording Cardiac Potentials", *Am. J. of Cardiology* 20:21–28, 1967. Fischmann, E., et al., "Beat to Beat and Observer Varation of the Electrocardiogram", *American Heart Journal* 75:465–473, 1968. Lauson. H., Bloomfield, R., Cournand, A., "The Influence of the Respiration on the Circulation in Man", *Am. J. of Medicine* 1:315–336, 1946. Starr, I., Friedland, C., "On the Cause of the Respiratory Variation of the Ballistocardiogram, with a Note on Sinus Arrhythmia", *J. of Clin. Investiation* 25:53–64, 1946. Melcher, A., "Respiratory Sinus Arrhythmia in Man", *Acta Physiologica Scandinavica* 435:6–25, 1976. In 1920, Bainbridge proposed that the greater the negative intrathoracic pressure generated by each inspiration, the greater the cardiac filling and quicker the subsequent pulse. Bainbridge, F. A., "The Relationship Between Respiration and the Pulse Rate", *J. Physiol.* 54:192–202, 1920.

Medical students have been taught for many decades that the sinus arrhythmia disappears with advancing age. Were this "disappearance" gradual rather than abrupt and quantifiable, it might provide a measure of cardiovascular physiologic age. Any index sensitive enough to accurately quantitate physiologic aging might also have uses in defining biologic effects of cardioactive drugs and cardiac toxins. Such an index must be equally useful in serially evaluating improvement or deterioration of cardiac tissue. Precise quantification of the sinus arrhythmia, however, has been hampered because the resiratory cycle and heart rate bear no *fixed* relationship to one another in the uncontrolled situation.

In 1963, a system called "Voluntary Cardiorespiratory Synchronization" (VCRS) was devised whereby breathing and heart rate could be voluntarily synchronized. This system was subsequently described in Almasi, J., Schmitt, O., "Basic Technology of Voluntary Cardiorespiratory Synchronization in Electrocardiology", *IEEE Transactions on Biomedical Engineering* 21:264–273, 1974. This system allows the subject to lock respiratory and heart rates in phase at a fixed integral ratio.

The principal features of the VCRS method used by Almasi and Schmitt included EKG leads which formed a pulse sensor, a current discriminator which counted successive electrical impulses which corresponded to sensed heart beats, and a ring counter which could be set to control light driver circuits at any desired ratio of sensed heart beats. The light driver circuits converted the desired pattern to a visual signal which advised the subject to inhale or exhale, each for the pre-selected number of beats. The system was "closed" when the subject voluntarily breathed according to these visual instructions. Thus respiration and heart beats were synchronized. If the subject could follow these simple visual instructions and the heart was in sinus rhythm, any reasonably comfortable pulse: inhale; pulse: exhale ratio could be achieved. The results of this VCRS method were recorded in the form of an EKG record. The VCRS circuit developed by Almasi and Schmitt has found no clinical application because the manual collection of instantaneous heart rate data from the cardiograph paper provides a record which is so cumbersome as to be completely useless in the clincal sense.

SUMMARY OF THE INVENTION

The present invention is an apparatus and method for measuring the condition of the cardiovascular system of a human subject. The present invention provides a precise and highly reproducible quantitative measurement of sinus arrhythmia.

In the present invention, pulse transducer means provides signal pulses representative of sensed heart beats of the human subject. Voluntary cardiorespiratory synchronization means provides stimulae to the human subject as a function of the signal pulses. The stimulae permit the human subject to voluntarily synchronize the subject's respiratory cycles with the heart beats, so that each respiratory cycle corresponds to a predetermined number N of heart beats. This voluntary synchronization is continued for a plurality of respiration cycles.

Instantaneous heart rate measurement means provides digital data which represents the instantaneous heart rate of each beat of the N-beat voluntarily synchronized respiratory cycles. This digital data is based upon the time interval between signal pulses.

The digital data are sorted by beat by data sorting means. Data analysis means analyzes the sorted digital data to derive one or more digital values indicative of a characteristic of the subject's cardiovascular system. Output means provides a human perceivable output as a function of the derived digital value. In preferred embodiments of the present invention, the data analysis means performs rhythomometric, statistical, and/or arithmetic analyses based upon the sorted digital data.

Most, if not all, biologic functions are rhythmic within many time frames. On the basis of period, rthythms can be separated into three domains: circadian (having a period of about twenty-four hours); infradian (having a period greater than twenty-eight hours); and ultradian (having a period less than twenty hours). The sinus arrhythmia is an example of a high frequency ultradian rhythm. The period of the sinus arrhythmia during voluntary synchronization corresponds to N heart beats (i.e. one respiration cycle).

In the embodiments of the present invention in which the data analysis means performs a rhythmometric analysis, the data analysis means first determines an average instantaneous heart rate for each heart beat of the respiratory cycle. The data analysis means then fits the average instantaneous heart rates to a cosine curve by least squares fitting procedures using single cosinor rhythmometric analysis. Based upon the cosine curve, the data analysis means determines rhythm parameter values, including a sinus arrhythmia amplitude value, a rhythm qualified mean heart rate (mesor), a timing value (acrophase) which indicates the location of the peak of the cosine curve in the respiratory cycle, and a percent rhythm value which indicates the quality of the fit of the cosine curve and the stored instanteous heart rates. An output is provided which can be compared to outputs from a wide variety of age, disease, and sex matched subjects as well as with outputs from previous determinations on the same subject. This output indicates the condition of the cardiovascular system of the human subject based upon the values derived from the rhythmometric analysis, particularly the sinus arrhythmia amplitude.

Equally valuable information may also be obtained when the data analysis means performs statistical analyses which include determination of the means and standard errors of instantaneous heart rate for each beat (1–N), an analysis of variance of these means, as well as creation and inspection of various sample arithmetic indices relating to these instantaneous heart rate means. One of these indices includes the computation of a modulation index. The data analysis means determine this modulation index by dividing the difference between the means of the highest and lowest instantaneous heart beat rates by the overall mean rate. For example, if "beat one" averaged a rate of 80 beats per minute and "beat four" averaged 60 beats per minute while the overall average rate during the recording span was 70 beats per minute, the modulating index (MI) would equal 80−60 or 20 divided by the average rate of 70 (20/70) or 0.29. Many other indices may also be created to relate directly measured values of instantaneous heart rate.

The present invention permits a precise and highly reproducible measurement of sinus arrhythmia amplitude. Utilizing the present invention, it has been determined that the measured sinus arrhythmia amplitude appears to provide indication of the compliance of the subject's heart tissue. The present invention provides a quantitative indication, therefore, of heat tissue compliance and thus the functional or physiological (as opposed to chronological) age of the subject's cardiovascular system.

Using the present invention, the effect of cardiotoxins on sinus arrhythmia amplitude has also been observed. The present invention makes it possible to monitor the effects of cardiotoxins cardioactive drugs and other substances on the cardiovascular system in a previously unavailable quantitative manner.

DETAILED DESCRIPTION OF THE PREFERRED EMBODIMENTS

Apparatus Description

In the present invention, instantaneous heart beat information obtained during voluntary cardiorespiratory synchronization is analyzed utilizing cosinor rhythmometric analysis and other analytic methods to provide an instantaneous, precise and highly reproducible assessment of sinus arrhythmia amplitude. It has been discovered that the sinus arrhythmia amplitude as measured utilizing the present invention decreases with advancing age, and thus provides a measure of cardiovascular physiological age. In addition, it has been found that the measured sinus arrhythmia amplitude is a sensitive indicator of the effects of substances such as cardiotoxins on the heart tissue.

The present invention, therefore, provides a quick, easy, reliable and totally noninvasive method of measuring cardiovascular conditions, with no risk of physical harm to the human subject. The ability to provide a quantitative measurement of sinus arrhythmia amplitude (as well as other parameters of cardiovascular performance), and the apparent direct relationship between that amplitude and heart tissue compliance provides a very wide range of applications for the present invention in medical practice, public health and health care maintenance.

Figure 1:
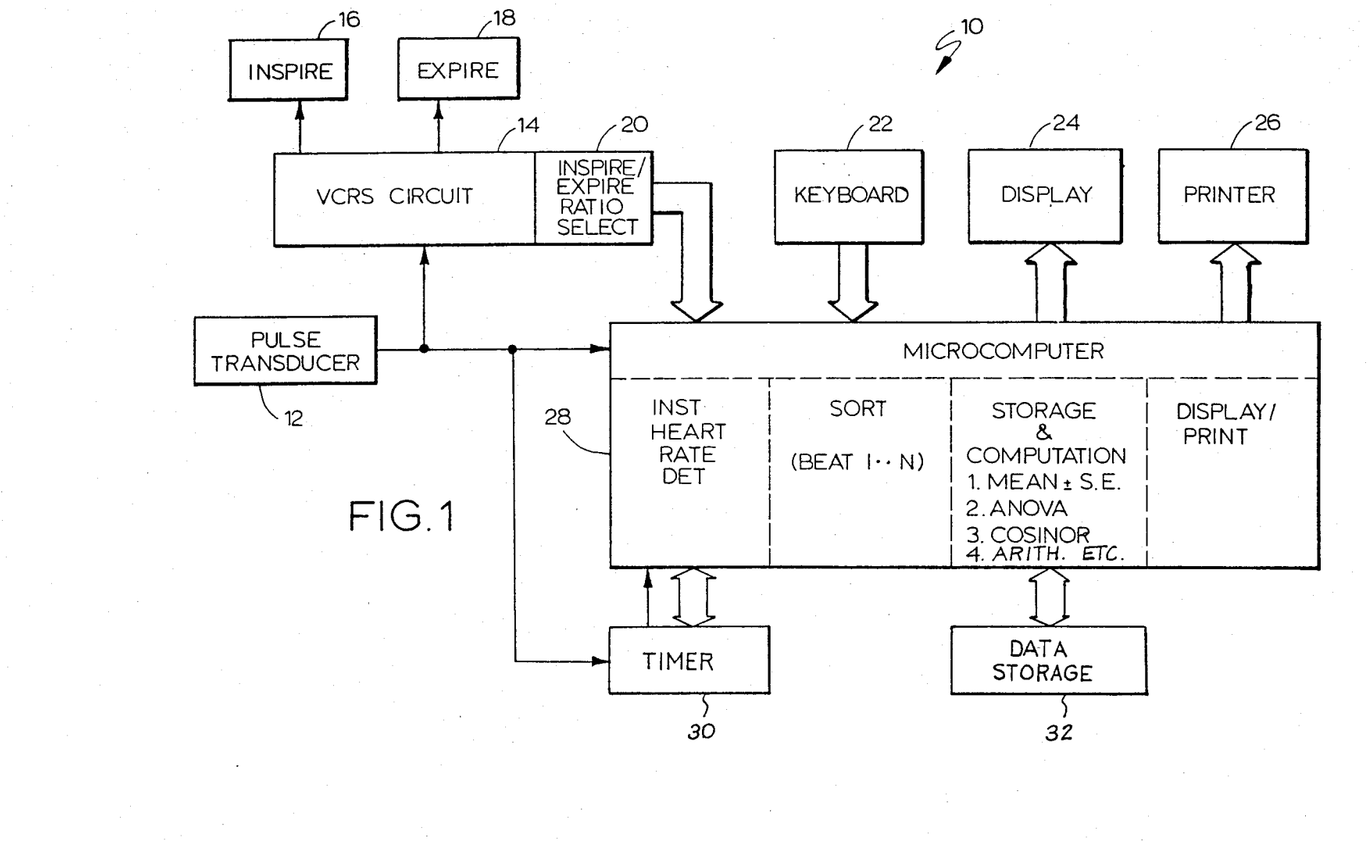
FIG. 1 is a block diagram of the preferred embodiment of the system of the present invention.

FIG. 1 shows a block diagram of sinus arrhythmia testing instrument 10 of the present invention. Instrument 10 includes pulse transducer 12, voluntary cardiorespiratory synchronization (VCRS) circuit 14, inspire indicator light 16, expire indicator light 18, inspire/expire ratio selector 20, keyboard 22, display 24, printer 26, microcomputer 28, timer 30, and data storage 32. Instrument 10 provides a quantitative analysis of sinus arrhythmia of a human subject while the subject is voluntarily synchronizing cardiac and respiratory cycles.

Pulse transducer 12 senses heart beats of the human subject. In preferred embodiments of the present invention, pulse transducer 12 is a simple, noninvasive type of pulse transducer, such as is used in coin-operated machines which measure pulse rates. With this type of pulse transducer, the human subject simply inserts a finger into a cavity in the pulse transducer. Other forms of pulse transducers, such as the electrodes and sensing circuitry of an electrocardiograph, can also be used, although this is less desirable since it involves attachment of electrodes to the subject's body.

The output of pulse transducer 12 is a signal which exhibits an electrical pulse corresponding to the occurrence of each heart beat. The output of pulse transducer 12 is provided to VCRS circuit 14, microcomputer 28 and timer 30.

VCRS circuit 14 operates in the manner described in the previously mentioned article by J. Almasi and O. Schmitt. The successive electrical pulses from pulse transducer 12 are counted by VCRS circuit 14, and drive signals are supplied to inspire indicator light 16 or expire indicator light 18. Inspire/expire ratio selector 20 (which in one embodiment is one or more user controlled switches), selects the ratio of heart beats for the inspiration and expiration portions of each respiratory cycle. In general, a ratio of two heart beats for inspiration to three heart beats for expiration appears to be relatively comfortable for the majority of human subjects. In subsequent discussion, the respiratory cycle having a total of five heart beats with a ratio of two beats inspiration (i.e. N132 2) to three beats expiration (i.e. N2=3) is used, but it will be understood that other numbers of beats and ratios are also possible.

The human subject is instructed to breathe in when the inspire indicator light 16 is turned on, and to breathe out when the expire indicator light 18 is turned on. This visually cued voluntary cardiorespiratory synchronization is achieved quite easily and comfortably by most human subjects within a very short time period (seconds).

Microcomputer 28 receives the output of pulse transducer 12 and preferably uses the signal pulses to maintain a count of the current beat in the cycle. The output from pulse transducer 12 is also provided to timer 30, which measures the time interval between successive signal pulses. Timer 30 preferably includes one or more counters which count in response to a high frequency clock signal. The signal pulse from pulse transducer 12 causes timer 30 to provide an interrupt signal to microcomputer 28. When each interrupt signal is received, microcomputer 28 reads the value in timer 30 and resets timer 30. The digital value from timer 30 represents the measured time interval.

In the preferred embodiment of the present invention, microcomputer 28 includes a microprocessor, read/write (RAM) data storage, read only memory (ROM) program storage, and interface circuitry required to interface microcomputer 28 with ratio selector 20, keyboard 22, display 24, printer 26, timer 30 and data storage 32. Microcomputer 28 receives the time interval data from timer 30 during a plurality of voluntarily synchronized respiratory cycles. Based upon this data, microcomputer 28 performs rhythmometric, nonrhythmometric statistical and arithmetic analyses to produce digital values which provide an indication of the condition of the human subject's cardiovascular system.

The functions performed by microcomputer 28 are indicated in the block diagram shown in FIG. 1. As interrupts from timer 30 are received, indicating each heart beat which has been sensed, microcomputer 28 determines the instantaneous heart rate. This is based upon the measured time interval between the previous heart beat and the just-recovered heart beat. Since this time interval represents the time required for one beat, microcomputer 28 calculates the instantaneous heart rate expressed, for example, as the number of beats per minute and stores that data in read/write storage.

The test continues for a selected period (such as one minute) during which a plurality of respiratory cycles occur. For example, if the average heart rate of the human subject over the one-minute time period is about seventy-five beats per minute, fifteen continuous synchronized respiratory cycles occur during that minute. Microcomputer 28 accumulates the instantaneous heart rate data for the selected time period, which may be a predetermined length of time, or a predetermined number of respiratory cycles. When the testing is complete, microcomputer 28 provides an indication to the human subject that the test is completed, e.g., through display 24. Alternatively, an audible signal indicating the completion of the test can be provided by microcomputer 28 by means of a sound transducer (not shown).

Once the instantaneous heart rate data has been obtained and stored, microcomputer 28 sorts the stored data into the respective first, second, third, fourth and fifth beats of the respiratory cycle. Microcomputer 28 knows the number N of beats in each cycle from the setting of inspire/expire selector 20. Microcomputer 28 then performs data analysis of the sorted data to produce digital values which provide an indication of cardiovascular performance during the synchronized respiratory cycles.

In the preferred embodiments, microcomputer 28 first performs a statistical analysis based upon the sorted data. Microcomputer 28 computes the mean and standard errors ("MEAN±SE") for the five beat categories using the stored data for those beat categories. Microcomputer 28 then performs an analysis of the variance (ANOVA) of the mean across the five beat categories. The result of this analysis by microcomputer 28 is an "f" value which indicates the amount of the variance of the mean and a "p" value which is a probability that the measured data is chance data. Both the mean and the standard error analysis and the analysis of variance of the mean are well known statistical analysis techniques. See, for example, Sokal, R. and Rohlf F., *Biometry, The Principles and Practice of Statistics in Biological Research*, Chapters 4 and 8 (1969).

Second, microcomputer 28 performs a single cosinor rhythmometric analysis. This analysis involves a least squares fit of a twenty-four hour cosine curve to the sorted instantaneous heart rate data. The results of the cosinor analysis are rhythm parameter values: a 5-beat mean heart rate value (mesor); a sinus arrhythmia amplitude which is half of the peak to trough difference of the fitted cosine curve; a timing value (acrophase) of the peak of the cosine curve in degrees or beats from the beginning of the five beat respiratory cycle; a percentage fit value; and 95% confidence level values. One preferred program used by microcomputer 28 to perform a cosinor analysis is described in Cornelissen, G., et al, "Chronobiometry with Pocket Calculators and Computer Systems", *La Ricera Clin. Lab.*, 10, 333 (1980). See also Halberg, F., "Auto-rhythmometry Procedures for Physiologic Self-measurements and Their Analysis", *Phsiol, Teach.* 1:1–11 (1972) for further description of cosinor analysis.

Third, microcomputer 28 performs an arithmetic analysis using either the mean values obtained during the statistical analysis of the rhythm parameters obtained during the rhythmometric analysis to derive one or more indices of cardiovascular performance. One example is a modulation index, which is derived by microcomputer 28 by subtracting the lowest from the highest mean instantaneous heart rate and dividing by an overall average rate. Another example is an index which is derived by microcomputer 28 by dividing the sinus arrhythmia amplitude value by the mesor value.

Fourth, in some embodiments of the present invention, microcomputer 28 statisically compares derived statistical, rhythm parameter or index values of the sorted data with previously stored values or data in data storage 32. These previously stored values or data are based upon earlier measurements of the same subject, and/or measurements from defined subsets of subjects of precise age categories, physical condition categories, disease categories, cardiotoxin exposure categories, or other drug exposure categories. This analysis, therefore, provides a comparison of the subject's most recent measurements with either his or her previous measurement or with those of similar subjects to provide an indication of how the subject has progressed over time or how the subject compares to others. One preferred statistical analysis performed by microcomputer 28 in this embodiment is the "Hotelling $T^2$ test". Hotelling, H., *Annals of Mathematical Statistics,* Volume 2, page 360 (1931).

Depending upon the volume of data to be stored, data storage 32 can take any one of several well-known forms. These include floppy disk storage, hard disk storage, or a separate main computer to which microcomputer 28 is linked. The storage data used by microcomputer 28 is selected based upon inputs from keyboard 22, which identify the subject and/or the subject's characteristics such as age, etc.

Fifth, in one preferred embodiment of the present invention, microcomputer 28 provides a digital value which represents the physiological (as opposed to chronological) age of the subject's cardiovascular system. As described in more detail later, the sinus arrhythmia amplitude value appears to provide a measure of heart tissue compliance which correlates well with physiological age. Microcomputer 28 derives a physiological age value from the amplitude value (or a derived index or combination of parameter values) and the chronological age of the subject entered through keyboard 22. A monogram stored in the form of a lookup table allows microcomputer 28 to derive a physiological age value, which is then displayed or printed.

Microcomputer 28 provides output information through display 24 and printer 26. The particular information to be displayed or printed is based upon instructions which are entered through keyboard 22. In preferred embodiments of the present invention, the information displayed or printed includes a depiction of the individual instantaneous heart rates measured for each of the five beats; the means and standard errors for each of the five beats; reconstructed cosine curves based upon the rhythm parameter values (which preferably include 95% confidence level depictions); numerical values of the mesor, the sinus arrhythmia amplitude, and the acrophase; a graphic or numerical comparison of the subject with the subject's earlier measurements or with measurements of others; and a numerical display of the physiological age of the heat tissue of the subject.

The present invention, therefore, can provide detailed data relating to a cardiovascular condition of the human subject in an extremely easy, safe, noninvasive, yet reliable manner. The entire testing to gather the data and the subsequent analysis by microcomputer 28 requires only a matter of a few minutes, including the training time for the human subject to synchronize his/her cardiorespiratory cycles.

The analyses performed by microcomputer 28 (MEAN±SE; ANOVA; COSINOR; ARITHMETIC; etc) do not require excessive memory capacity. Nor do the functions of determining instantaneous heart rate, sorting the data into heart beat groups, and the displaying and printing require excessive memory capacity. As a result, the entire system 10 is capable of incorporation in a compact, desk top test instrument. The relatively small size, speed and ease of use of the system 10 of the present invention make its use attractive in a wide variety of medical public health and health care maintenance applications.

Test Results

In tests performed using voluntary cardiorespiratory synchronization and subsequent statistical and rhythmometric analyses, it has been determined that the sinus arrhythmia amplitude, which is derived from the cosinor analysis, is an easily measured index of cardiac function which correlates well in an inverse relationship with cardiovascular physiological age. These tests have shown that the sinus arrhythmia amplitude has little test-to-test variability with the same individual human subjects. The amplitude and timing of the peak of the 5-beat rhythm have been found to change predictably with age. In particular, the sinus arrhythmia amplitude has been found to decrease approximately 10 percent per decade between ages twenty and eighty-two, from about 10.8 percent to about 4.4 percent of the mean heart rate.

In this testing, heart beats of the subjects were sensed during voluntary cardiorespiratory synchronization. The instantaneous heart rates were calculated, sorted, and subjected to single cosinor analysis to derive a mesor, amplitude, and acrophase for that subject. Population mean cosinor analysis was then used to combine these parameters from the data series for subsets of the subjects studied. This form of analysis investigates whether rhythm characteristics are consistent among individuals in the group. If individual means, amplitudes, and timings of peak values differ substantially, a statistically significant population mean rhythm will not be indicated. For end points characterized by statistically significant (p less than 0.05) population rhythms, the Hotelling $T^2$ (or Bingham) test was used to compare rhythm parameters (singly and in combination) between data series obtained from different groups of subjects or from the same subjects at differing times. Multivariate analysis was used to complement Bingham testing. Linear regression analysis was used to inspect for trends in data due to age or Doxorubicin dosage while correlation coefficients were calculated to relate trends.

In order to investigate intra individual variability and the effect of advancing age on sinus arrhythmia, twenty-five presumably healthy (i.e. no history of cardiovascular disease and taking no medication) subjects of both sexes from twenty to eighty-two years of age were studied at 7 a.m. and 9 a.m., before and after diagnostic venipunctures. The twenty-five healthy subjects showed a stability of the average heart rate, the amplitude of sinus arrhythmia, and the timing of the highest instantaneous heart rate within the five beat rhythm. No statistical difference characterized the rhythms of these twenty-five subjects before and following venopuncture.

Figure 2:
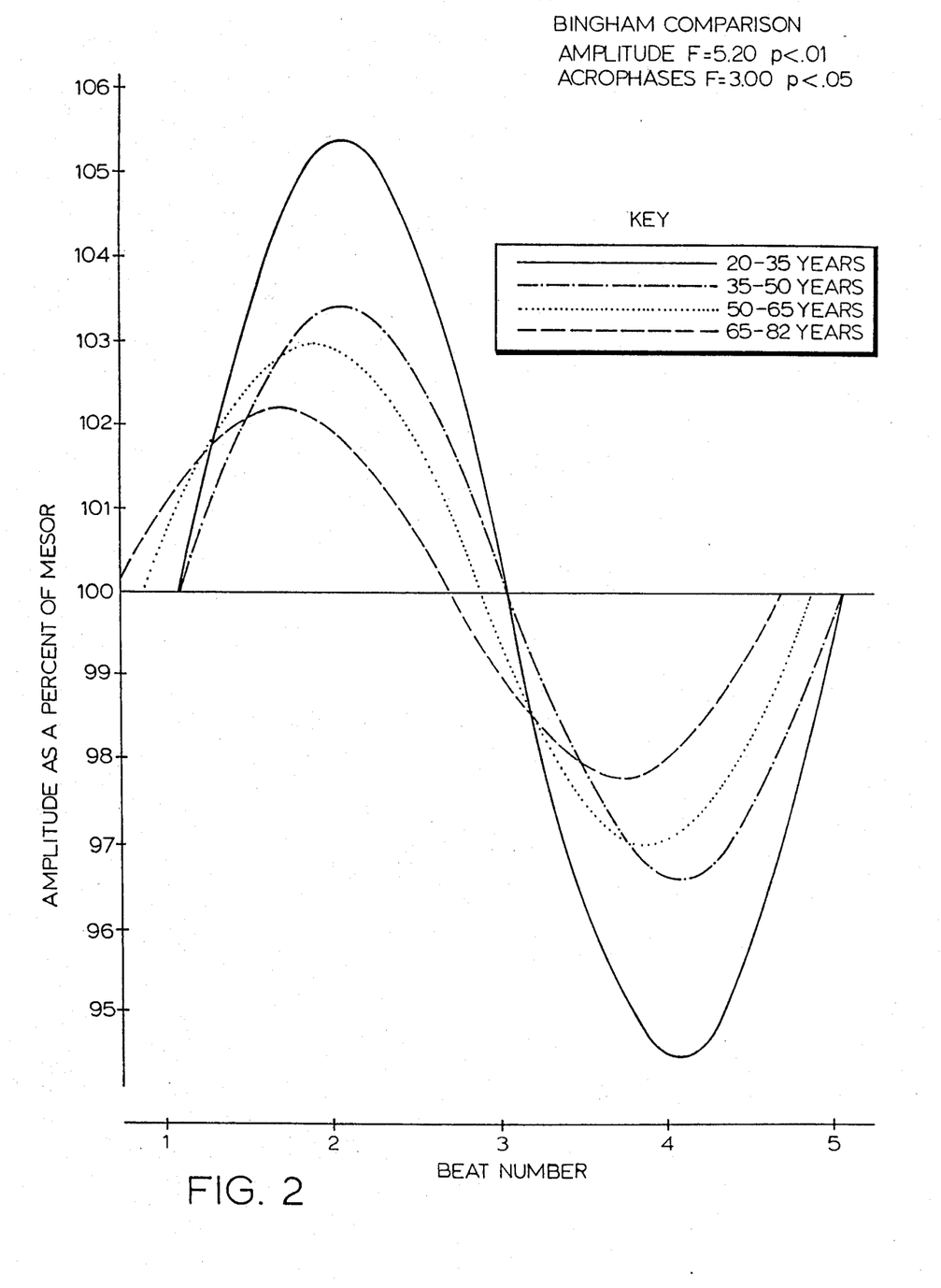
FIG. 2 is a graph of amplitude as a function of beat number which illustrates the effect of age on sinus arrhythmia.

The twenty-five healthy subjects were arbitrarily placed into one of four age categories, each spanning approximately fifteen years (20–35; 35–50; 50–65; and 65–82). Every individual and each age defined population were found to have highly statistically significant five beat rhythms. These age defined populations demonstrated an age dependent decrease in sinus arrhythmia amplitude and a shift in peak timing, whether the data were expressed in absolute terms (beats per minute) or in a relative manner (amplitude as a percentage of mean). The absolute sinus arrhythmia fell from nearly four beats per cycle in the youngest group of subjects to just over 1.3 beats per cycle in the oldest age group. FIG. 2 is a graph of composite cosine curves for the four age groups, which show the age dependent changes in sinus arrhythmia. As seen in FIG. 2, the youngest group (20–35 years) exhibited the largest amplitude and the latest peak, while the oldest group (65–82 years) showed the lowest amplitude and the earliest peak. As age increases, the timing of the peak shifts linearly to earlier beats of the 5-beat cycle.

Figure 3:
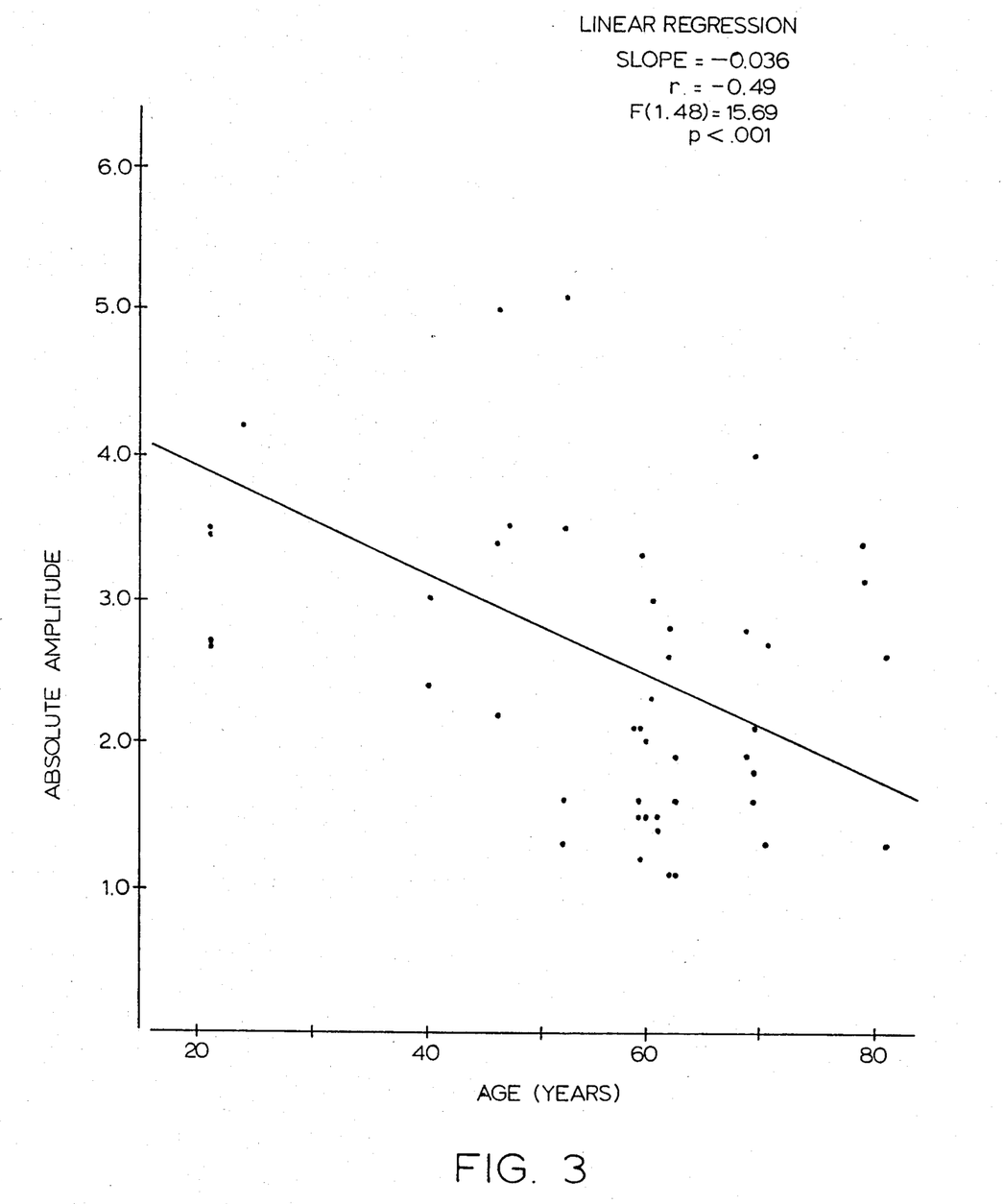
FIG. 3 is a graph of sinus arrhythmia amplitude as a function of age.

Linear regression analysis of the change in amplitude with advancing age shows a linear fall, as shown in FIG. 3. Extension of this regression line reveals that the maximum extent of rhythmic variation is around twelve percent of the mean heart rate, and that the amplitude disappears at about the age of 120 years.

Figure 4:
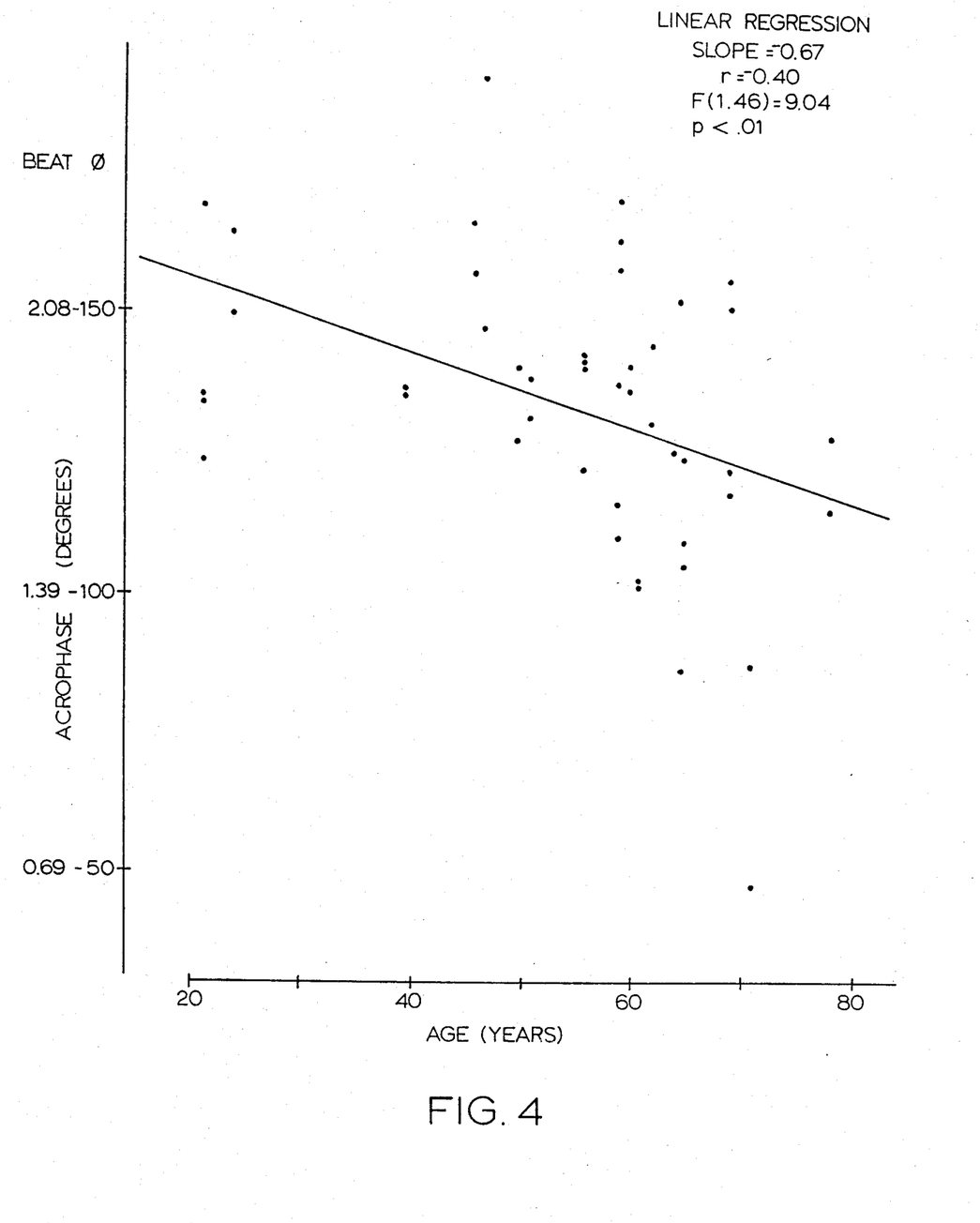
FIG. 4 is a graph of sinus arrhythmia pulse rate timing (acrophase) as function of age.

FIG. 4 shows the results of linear regression analysis of the decrease of acrophase with advancing age.

With the method of the present invention, the mechanisms of the sinus arrhythmia were studied by comparing the sinus arrhythmia of two unusual experimental subjects with that of age-matched control subjects. The first experimental subject was a forty-four year-old man who had received a cardiac transplant several days prior to study. The heart was taken from a thirty-five year-old male accident victim. All sympathetic and parasympathetic nervous connection was, of course, interrupted during extirpation of the heart. The second experimental subject was a forty-seven year-old female with a twenty year history of poorly controlled diabetes. The subject suffered from moderate orthostatic hypotension, severe symptomatic peripheral neuropathy, mild enteropathy, mild kidney dysfunction with albuminuria and diabetic retinal changes. Each of these subjects were studied in order to further illucidate the importance of an intact nervous system to the sinus arrhythmia.

In the past, local and central nervous reflex arcs have been implicated as important components of the sinus arrhythmia. The first subject, who was studied after a recent heart transplantation, serves as an example in which all central nervous system cardiac communication has been surgically severed. The second subject with diabetic peripheral sympathetic and visceral neuropathy serves as an example in which all small nerves have presumably been damaged by a longstanding metabolic abnormality, as well as perhaps by chemotherapy for her ovarian cancer. If sympathetic-parasympathetic cardiac innervation is necessary for the manifestation of the sinus arrhythmia each of these subjects should have severely abnormal sinus arrhythmia patterns.

Figure 5:
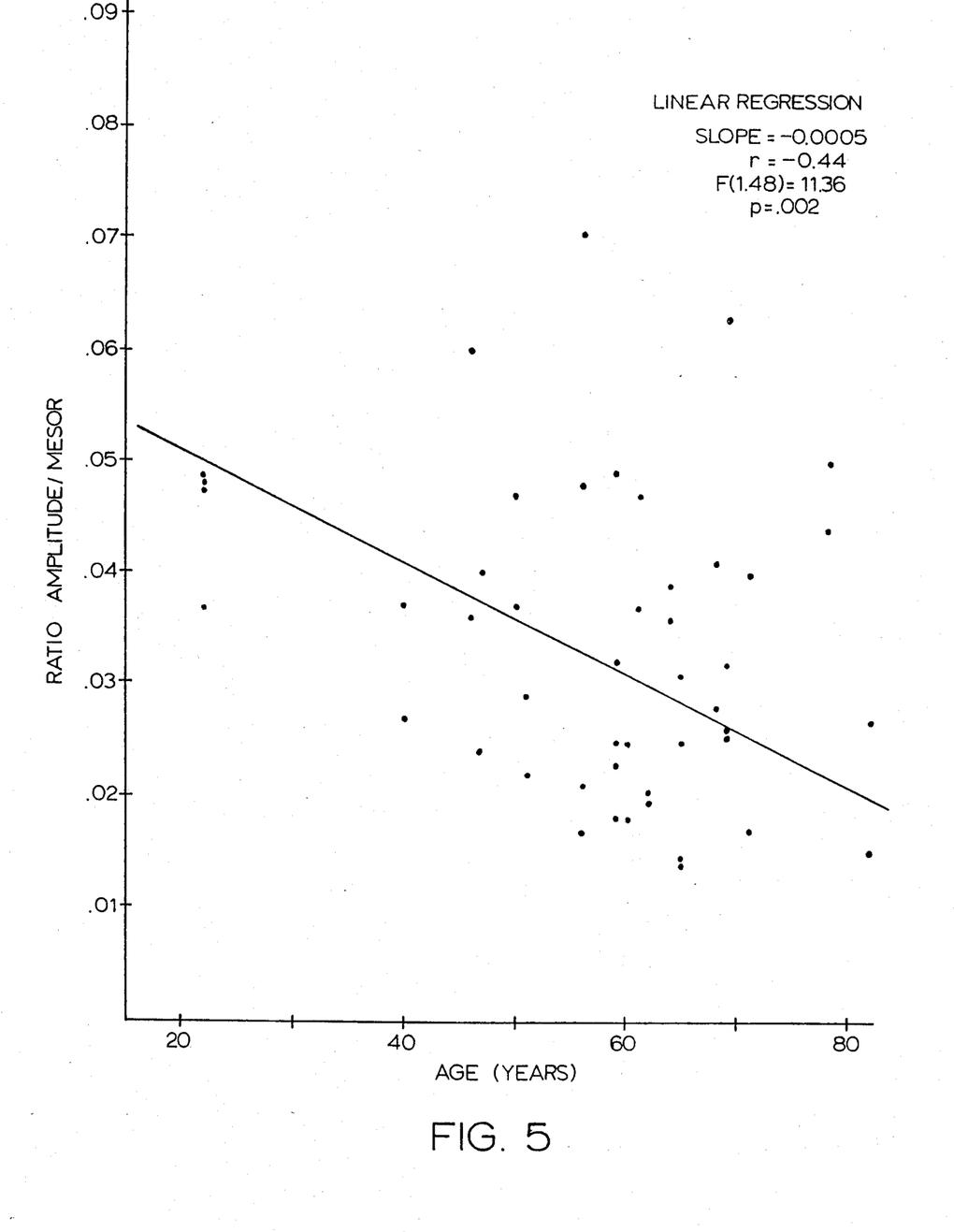
FIG. 5 is a graph of the ratio of sinus arrhythmia amplitude to overall mean heart rate (mesor) as a function of age of the subject.

The first experimental subject (with the transplanted heart) was studied shortly after removal of all chest tubes. Within a week of this major surgery, he felt well and cardiorespiratory examination was normal. The subject followed instructions well, but the depth of inspiration was somewhat limited by pain from recent median sternotomy. A statistically significant "sinus arrhythmia rhythm" was present in this subject without cardiac innervation. The sinus arrhythmia amplitude of this rhythm was 1.7 beats per minute and the peak occurred between the first and second beats of the 5-beat cycle. FIG. 5 is a graph comparing the sinus arrhythmia in the first experimental subject to the mean sinus arrhythmia rhythm of a group of five age-matched control subjects. The timing of the sinus arrhythmia rhythm of the first experimental subject is precisely the same as the control populations while the amplitude is somewhat lower, perhaps the result of decreased inspiratory effort due to post-operative pain.

The second experimental subject (with diabetic neuropathy) had also been treated with seven courses of chemotherapy (Doxorubicin or "ADR"). At the time of sinus arrhythmia measurement using the method of the present invention, the second experimental subject had no clinical or laboratory evidence of Doxorubicin-induced cardiac damage. A history of mild orthostatic hypotension; intermittent nausea, vomiting, and diarrhea; and severe numbness of fingers and feet to the level of the knee with complaints of not being able "to tell where her feet were" was elicited. Physical examination revealed a resting tachycardia, 116/minute, a 20 mm of mercury drop in diastolic blood pressure upon standing, retinal arteriolar narrowing and tortuosity, severe stocking-glove loss of pain, light touch and vibration sensation in all four extremities, worse in lower extremities. Urinalysis revealed glucosuria and 2+ albuminuria, a creatinine clearance of 60 cc/minute and fasting blood glucose was usually between 250–500 mg%.

The measured sinus arrhythmia for the second experimental subject showed a statistically significant 5-beat rhythm. The amplitude of the rhythm was 1.9 beats per minute compared to the 1.3 beats per minute amplitude of a control subject matched for age, sex, clinical cardiac status, and total Doxorubicin dosage. The timing of the peak for the control subject was between the first and second while that of the diabetic subject was between the second and third beats of the 5-beat cycle. Since the heart rate of the diabetic subject was much higher than that of the control subject, the amplitude relative to the mean heart rate was somewhat, but not significantly, larger than that of the control subject.

Figure 6:
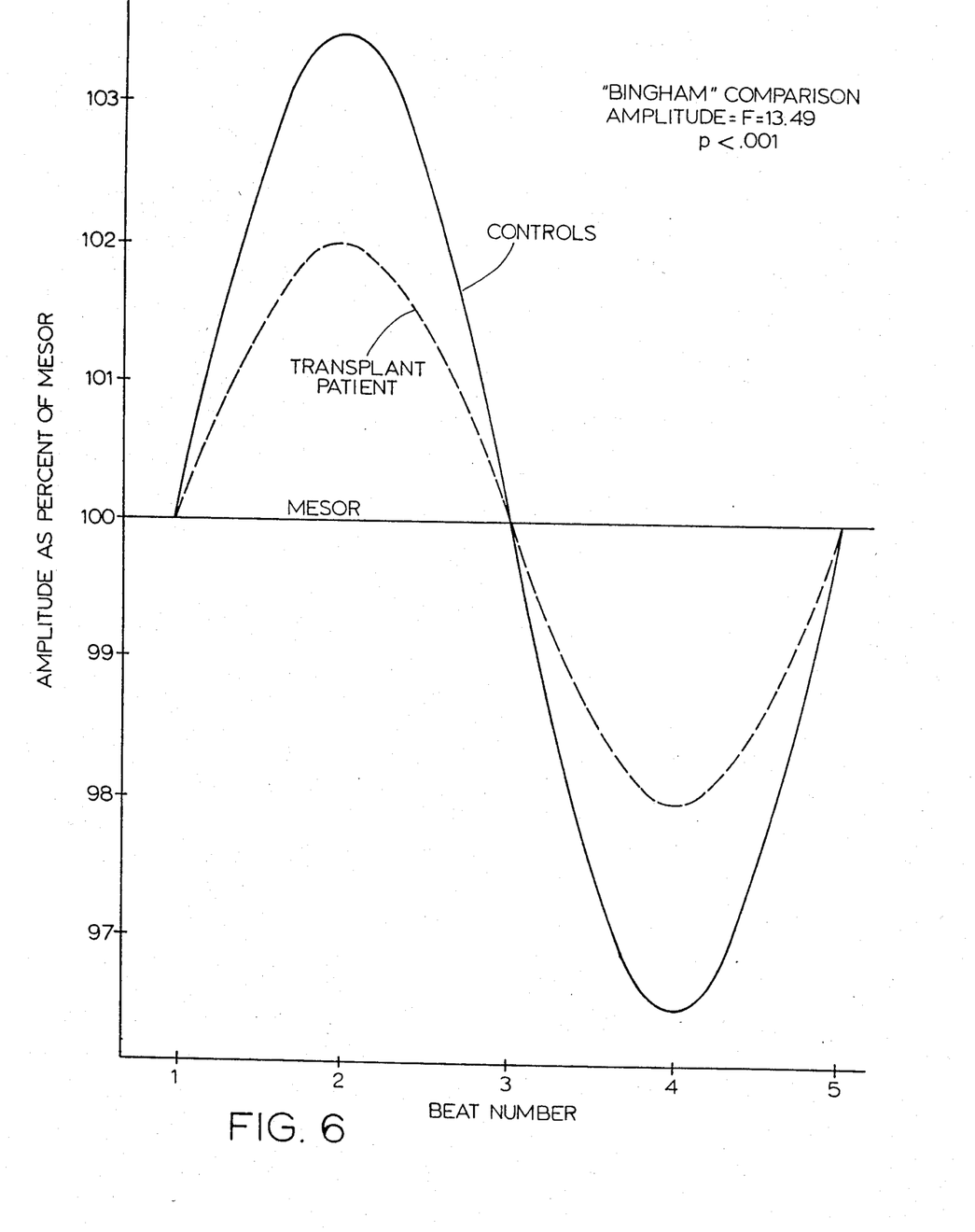
FIG. 6 is a graph of sinus arrhythmia amplitude as a function of beat number illustrating the effects of heart transplantation on sinus arrhythmia.

Doxorubicin (ADR), a potent cardiotoxin used in cancer chemotherapy, causes a serious and often fatal cardiomyopathy. It damages the heart in a total dose-dependent fashion. The sinus arrhythmia was measured immediately before and one hour after 60 mg/m$^2$ of body surface area of Doxorubicin was given to patients with advanced cancer. FIG. 6 compares these results to the sinus arrhythmia of the thirty-eight age-matched data series from healthy subjects.

The sinus arrhythmia of patients who were about to receive Doxorubicin was highly rhythmic and did not differ from the sinus arrhythmia of the control population. In these same individuals, Doxorubicin caused the sinus arrhythmia rhythm to disappear. The sinus arrhythmia amplitude fell by nearly ten fold to undetectable levels. Longitudinal follow-up was possible in two of the patients, one at twenty-four hours and the second one month after Doxorubicin. The disappearance of sinus arrhythmia amplitude persisted for twenty-four hours, but the sinus arrhythmia amplitude returned to near pretreatment levels by one month following Doxorubicin.

The chronic administration of Doxorubicin is known to cause total dose-dependent cardiac dysfunction. This was studied using the present invention by comparing the 5-beat sinus arrhythmia rhythm characteristics of thirty-eight data series from age matched healthy subjects with those of six patients who had received two to six courses of monthly Doxorubicin and with those of six patients who had received greater than six courses of Doxorubicin. No patient had received Doxorubicin for a minimum of thirty days prior to sinus arrhythmia testing and no patient had symptoms of heart disease.

Figure 7:
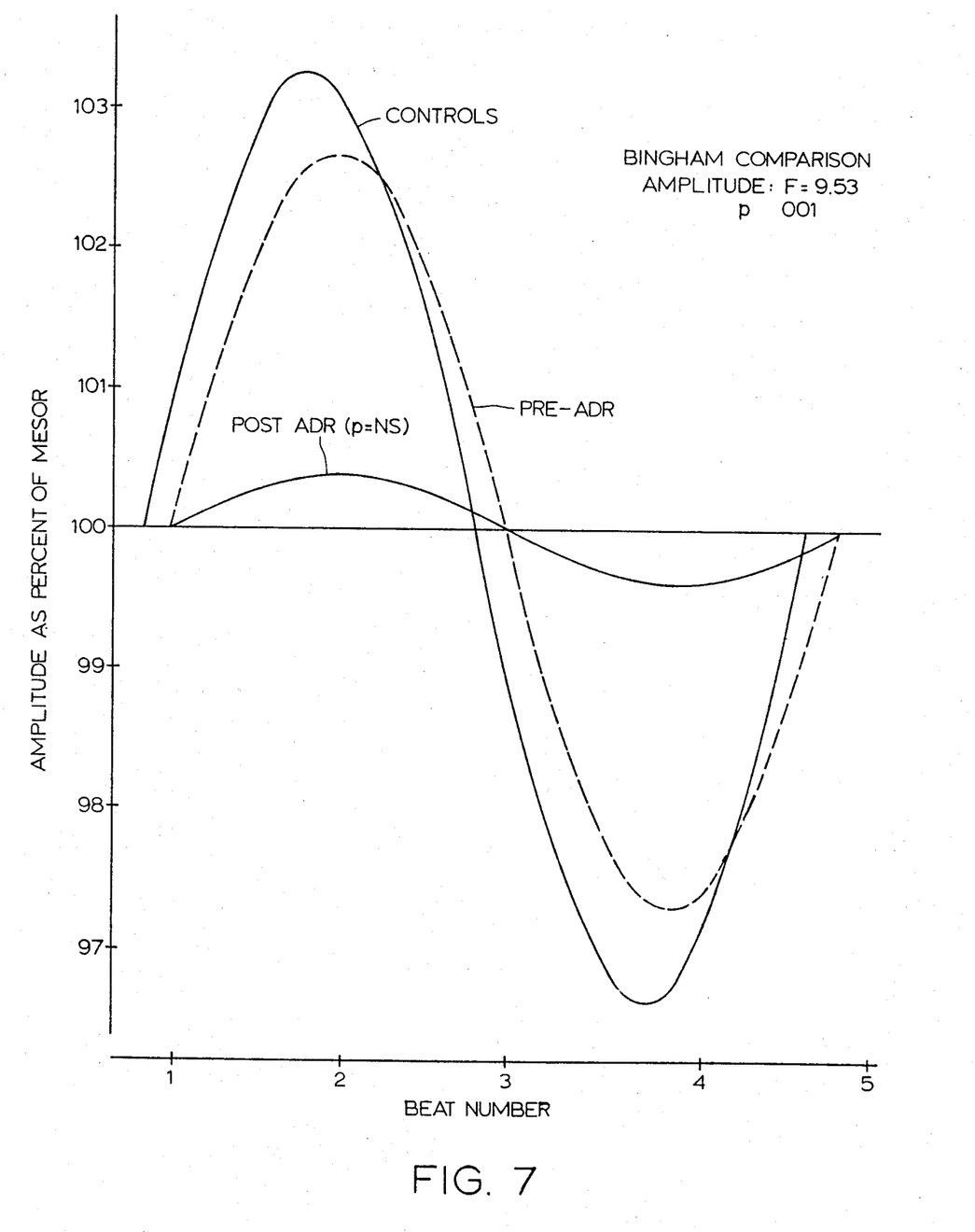
FIG. 7 is a graph of amplitude as a function of beat number illustrating the acute effect of Doxorubicin (a cardiac poison) on sinus arrthythmia.

Statistical evaluation of sinus arrhythmia revealed that little change characterized those subjects who had received fewer than six courses of chemotherapy. The 5-beat sinus arrhythmia rhythm disappeared, however, in the group of asymptomatic patients who had received more than six courses of Doxorubicin therapy. These findings are represented by reconstructed curves in FIG. 7.

Figure 8:
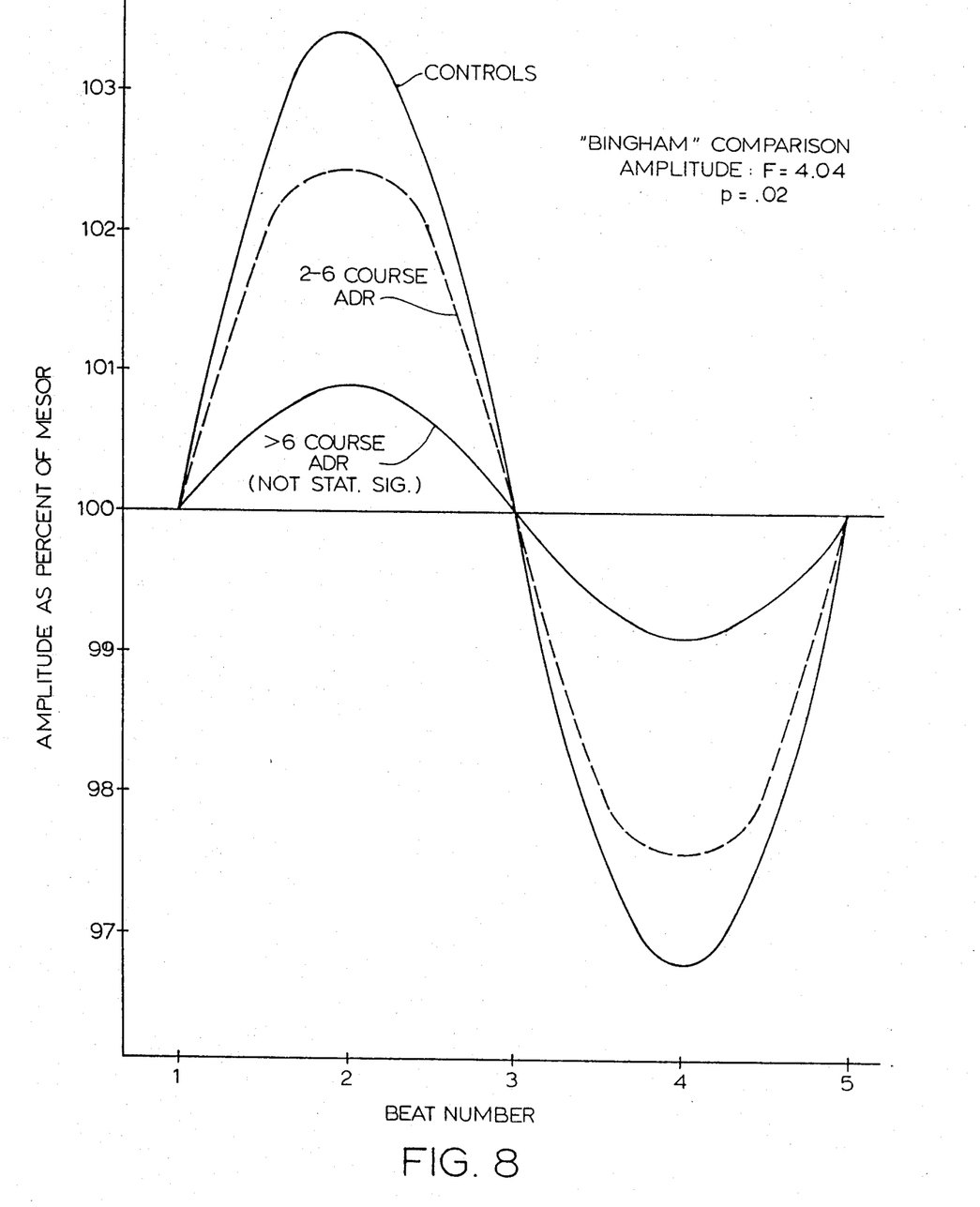
FIG. 8 is a graph of sinus arrhythmia amplitude as a function of beat number showing the chronic effects of Doxorubicin on sinus arrhythmia.

The rhythm characteristics of the sinus arrhythmia from a group of forty-four data series from age matched healthy subjects were compared to those from a group of subjects who had received 550 mg/m$^2$ of Doxorubicin either with (n=4) or without (n=3) historical, physical examination or laboratory evidence of Doxorubicin-induced cardiac damage. 550 mg/m$^2$ of Doxorubicin caused destruction of the group sinus arrhythmia rhythm in both groups indicating the possible sensitivity of this index to both clinical and subclinical cardiac injury. When individual sinus arrhythmia rhythms were evaluated, however, each of the three subjects without clinical heart damage had statistically significant sinus arrhythmia rhythms, while each of the four subjects suffering from clinical heart damage had lost statistically significant 5-beat sinus arrhythmia rhythms. See FIG. 8. These findings indicate that the individuals' sinus arrhythmia rhythm characteristics become dyssynchronous both prior to their disappearance and prior to the appearance of clinical heart damage.

Conclusion

The effects of respiration upon heart rate have been noted since 1733. Kymograph recordings of concurrent heart beat and breathing pattern emphasize the apparent regularity of this relationship in the mid nineteenth century. Since the first recording of the electrical activity of the heart by means of the electrocardiograph, respiratory influences have been noted by many researchers. Deep breathing and breath holding techniques have failed to regularize the heart rhythm. Even breathing with a timing device does not succeed in fixing the relationship between pulse and the respiratory cycle.

The present invention utilizes voluntary cardiorespiratory synchronization, the determination of instantaneous heart rate for each heart beat over a plurality of synchronized respiratory cycles, and the statistical and rhythmometric analysis of the instantaneous heart rates sorted by beat. With the present invention, quantification of parameters of the resultant synchronized sinus arrthythmia is achieved.

Using the present invention, sinus arrhythmia becomes an easily measured index of cardiac function whose amplitude correlates inversely with advancing age. This index has little test-to-test variability within the same individuals. The amplitude and timing of the peak of the 5-beat sinus arrhythmia rhythm both change predictably with age. In addition, tests have shown that the sinus arrhythmia measured with the present invention is sensitive to the acute and chronic administration of a cardiac poison which causes cumulative heart toxicity.

It is likely that ventricular compliance is the primary variable being measured by the present invention. The more supple the ventricle, the more brisk its filling and subsequent emptying in response to negative pressure induced venous filling increase. As the ventricle ages, its suppleness decreased, which changes the sinus arrhythmia amplitude and acrophase predictably. If injured by ischemia, iron overload or by a cardiotoxin, if affected by a cardiosuppressive drug; the suppleness of the ventricle may be decreased causing a predictable decrease in sinus arrhythmia amplitude. Likewise, a program of increasing graded aerobic exercise or the admininstration of a cardiotonic agent may increase ventricular suppleness and thus increase the sinus arrhythmia amplitude.

Using the present invention, a nomogram has been constructed on which sinus arrhythmia amplitude and chronologic age are aligned. By connecting the amplitude of the measured sinus arrhythmia amplitude with the subject's chronologic age, his or her physiologic cardiac age can be estimated. The nomogram is, in a preferred embodiment, stored in the form of a lookup table or formula by microcomputer 28. The subject's chronologic age is entered through keyboard 22. Based upon the measured sinus arrhythmia amplitude and the chronologic age entered through keyboard 22, microcomputer 28 retrieves from the lookup table the estimated physiologic cardiac age, and displays that information on display 24. For example, a thirty-year old person with a stiff ventricle and subsequently a low sinus arrhythmia amplitude of 1.0 (perhaps secondary to multiple myocardial infarctions, chronic ischemia, hypothyroidism, hemachromatosis, therapuetic intramyocardial quinidine sulfate levels or Doxorubicin therapy) will have a cardiophysiologic age of 55-60 years. By use of the present invention over a period of time, the subject can longitudinally monitor the effects of therapeutic maneuvers which decrease ischemia, correct hypothyroidism, decrease iron overload, remove quinidine, or reverse Doxorubicin damage. A favorable result will be either an increase in sinus arrhythmia amplitude as measured using the present invention, or at least a decrease in the rate of decline of the sinus arrhythmia amplitude over time.

The present invention, which provides a fast and simple, yet sensitive quantitative measure of sinus arrhythmia parameters has wide applicability. First, the present invention is useful in the quantification of physiologic cardiovascular age. Applications include the objective study of aging; sports medicine; physical training; exercise physiology; cardiac rehabilitation; preventive medicine; and general health maintenance. By use of the present invention over a period of time, a subject or his physician can monitor the condition of the subject's heart and the effects of training or other measures intended to improve cardiovascular condition.

Second, the present invention is useful in the field of toxicology, particularly in the study of the effect of cardiotoxins. This includes the study of the effects of poisonous anticancer drugs; the screening of classes of substances to determine their potential cardiotoxicity; and the quantitation of cardiotoxin effects.

Third, the present invention is useful in the field of clinical pharmacology as it relates to cardiac drugs. By use of the present invention, it is possible to measure the biological effect of particular drugs on the cardiovascular system. Because the present invention is a quick totally noninvasive and easy test which provides results within a short time period, a succession of tests can be performed to study the effect of a drug over a period of time.

Fourth, the present invention is applicable to the field of endocrinology. The effect of hormone levels on sinus arrhythmia, and in particular cardiovascular compliance can be monitored using the present invention.

Fifth, the present invention has broad applications in the field of basic cardiovascular physiology. Although the effects of sinus arrhythmia have been noted for over 250 years, the precise mechanisms involved are still not fully understood. As described previously, the study of sinus arrhythmia using the method of the present invention with both normal subjects and subjects having unusual conditions (for example the heart transplant subject) provides information which leads to a more complete understanding of the cardiovascular system.

Although the present invention has been described with reference to preferred embodiments, workers skilled in the art will recognize that changes may be made in form and detail without departing from the spirit and scope of the invention.

What is claimed is:

1. An apparatus for noninvasive quantitative measurement of characteristics of a cardiovascular system of a human object, the instrument comprising:
noninvasive pulse transducer means for providing signal pulses representative of sensed heart beats of the human subject;
voluntary cardiorespiratory synchronization means responsive to the signal pulses for providing stimulae which permit the human subject to voluntarily synchronize the subject's respiratory cycles with the subject's heart beats;
instantaneous heart rate measurement means responsive to the signal pulses for providing digital data representative of instantaneous heart rate at each heart beat of a plurality of N-beat voluntarily synchronized respiratory cycles;
data sorting means for sorting the digital data by each of N-beat categories;
data analysis means for analyzing the sorted digital data to derive a digital value indicative of a characteristic of the subject's cardiovascular system; and
output means for providing a human perceivable output as a function of the derived digital value.

2. The apparatus of claim 1 wherein the data analysis means comprises:
means for computing a mean and a standard error digital value for each beat category based upon the sorted digital data.

3. The apparatus of claim 2 wherein the data analysis means further comprises:
means for computing a digital value for each beat category representative of variance of the main.

4. The apparatus of claim 2 wherein the data analysis means further comprises:
means for computing an index representative of a characteristic of the subject's cardiovascular system based upon the mean digital values.

5. The apparatus of claim 4 and further comprising:
input means for providing an input signal indicative of chronologic age of the subject;
means for deriving a digital value representative of physiologic age of the subject's cardiovascular system based upon the index and the input signal; and
wherein the output means provides a human perceivable output repesentative of the derived physiologic age.

6. The apparatus of claim 1 wherein the data analysis means comprises:
means for deriving a cosine curve which best fits the sorted digital data;
means for determining rhythm parameter values based upon the cosine curve; and
wherein the output means provides the human perceivable output as a function of the rhythm parameter values.

7. The apparatus of claim 6 wherein the output means provides a reconstructed visual representation of the cosine curve based upon the rhythm parameter values.

8. The apparatus of claim 7 wherein the rhythm parameter values include confidence intervals, and wherein the reconstructed visual representation of the cosine curve includes a representation of the confidence intervals.

9. The apparatus of claim 6 wherein the rhythm parameter values include an amplitude value.

10. The apparatus of claim 9 wherein the rhythm parameter values include a mean instantaneous heart rate value.

11. The apparatus of claim 10 wherein the rhythm parameter values include a timing value representative of a location of a peak of the cosine curve.

12. The apparatus of claim 6 and further comprising:
means for computing an index representative of a characteristic of the subject's cardiovascular system based upon the rhythm parameter values; and
wherein the output means provides a human perceivable output as a function of the index.

13. The apparatus of claim 6 and further comprising:
input means for providing an input signal indicative of chronologic age of the subject; and
means for deriving a digital value representative of physiologic age of the subject's cardiovascular system as a function of the input signal and a rhythm parameter value.

14. The apparatus of claim 1 wherein the data analysis means derives a plurality of digital values, and wherein the apparatus further comprises:
means for selecting at least one of the plurality of digital values as the digital value upon which the human perceivable output is based.

15. The apparatus of claim 14 wherein the data analysis means comprises:
statistical analysis means for deriving a plurality of statistical values based upon the sorted digital data; and
rhythmometric analysis means for deriving a plurality of rhythm parameter values based upon the sorted digital data.

16. The apparatus of claim 15 wherein the data analysis means further comprises:
arithmetic analysis means for deriving an index value based upon a plurality of the derived values.

17. The apparatus of claim 1 and further comprising:
data storage means for storing data representative of previous testing; and
wherein the data analysis means analyzes the sorted digital data and the stored data to produce the digital value indicative of the characteristic of the subject's cardiovascular system, and wherein the digital value is representative of a comparison of a current state of the subject's cardiovascular system with results of the previous testing.

18. The apparatus of claim 17 wherein the data stored by the data storage means is representative of previous testing of the subject.

19. The apparatus of claim 17 wherein the data stored by the data storage means is representative of previous testing of a subset of subjects having a characteristic in common with the subject.

20. An apparatus for noninvasive quantitative measurement of characteristics of a cardiovascular system of a human subject, the apparatus comprising:
noninvasive pulse transducer means for providing signal pulses representative of sensed heart beats of the human subject;
voluntary cardiorespiratory synchronization means responsive to the signal pulses for providing stimulae which permit the human subject to voluntarily synchronize the subject's respiratory cycles with the subject's heart beats so that each respiratory cycle has a period corresponding to a predetermined number N of heart beats;
instantaneous heart rate measurement means for providing digital data representative of instantaneous heart rate at each sensed heart beat based upon the signal pulses;
means for storing the digital data for each sensed heart beat during a plurality of N-beat voluntarily synchronized respiratory cycles;
statistical analysis means for deriving a plurality of digital statistical values based upon the digital data;
rhythmometric analysis means for deriving a plurality of digital rhythm parameter values based upon the digital data; and
means for providing an output signal based upon at least one digital value derived from the digital data.

21. The apparatus of claim 20 and further comprising:
data sorting means for sorting the digital data by each beat of the N-beat respiratory cycles; and
wherein the statistical analysis means and the rhythmometric means derive the digital values as a function of the sorted digital data.

22. The apparatus of claim 21 wherein the statistical analysis means derives a mean and standard error value for each of the N beats as a function of the sorted digital data.

23. The apparatus of claim 22 wherein the statistical analysis means also derives a digital value representative of variance of the mean for each of the N beats.

24. The apparatus of claim 20 wherein the rhythmometric analysis means derives a cosine curve which best fits the digital data and determines the rhythm parameter values from the derived cosine curve.

25. The apparatus of claim 24 wherein the rhythm parameter values include an amplitude value, a mean instantaneous heart rate value and a timing value.

26. The apparatus of claim 20 and further comprising:
display means for displaying a visual output as a function of the output signal.

27. The apparatus of claim 20 and further comprising:
data storage means for storing previous test data representative of results of previous testing; and
means for providing a digital value representative of a comparison of the previous test data and digital data corresponding to a current measurement of the subject.

28. The apparatus of claim 27 wherein the previous test data is representative of previous testing of the subject.

29. The apparatus of claim 27 wherein the previous test data is representative of previous testing of a subset of subjects having a characteristic in common with the subject.

30. A noninvasive method of measuring condition of the cardiovascular system of a human subject, the method comprising:
providing a signal pulse in response to each sensed heart beat of the human subject;
providing stimulae to the human subject, as a function of the signal pulses, which stimulae permit the human subject to voluntarily synchronize the subject's respiratory cycles with the subject's sensed heart beats, so that a first number N1 of heart beats occur during an inhalation portion of each N-beat respiratory cycle and a second number N2 of heart beats occur during an expiration portion of each N-beat respiratory cycle;
determining, based upon time intervals between the signal pulses, instantaneous heart rates for each sensed heart beat during a plurality of voluntarily synchronized N-beat respiratory cycles;

deriving a cosine curve which best characterizes the instantaneous heart rates during the voluntarily synchronized N-beat cycles; and providing an output signal based upon the derived cosine curve.

31. The method of claim 30 wherein providing an output comprises:

determining an amplitude value as a function of a minimum and a maximum of the cosine curve; and providing the output signal as a function of the amplitude value.

32. The method of claim 30 wherein providing the output signal comprises:

determining a timing value representative of a location of a peak of the cosine curve; and providing the output signal as a function of the timing value.

33. The method of claim 30 wherein providing the output signal comprises:

determining a mean instantaneous heart rate value for the N-beat respiratory cycle; and providing the output signal as a function of the mean instantaneous heart rate value.

34. The method of claim 30 wherein deriving a cosine curve comprises:

sorting the instantaneous heart rates by each beat of the N-beat respiratory cycles;

performing a cosinor rhythmometric analysis of the sorted instantaneous heart rates to derive a cosine curve which best fits the sorted instantaneous heart rates.

35. The method of claim 30 and further comprising:

determining for each beat of the N-beat respiratory cycle a mean instantaneous heart rate value and a standard error value based upon the instantaneous heart rates corresponding to that beat; and providing an output signal which is a function of the mean instantaneous heart rate values and the standard error values.

* * * * *